United States Patent [19]
Wolff

[11] Patent Number: 4,835,400
[45] Date of Patent: May 30, 1989

[54] RECLINER PANE FOR TANNING APPARATUS

[76] Inventor: Friedrich Wolff, Störklingasse 44, CH-4125 Riehen/Basel, Switzerland

[21] Appl. No.: 100,018

[22] Filed: Sep. 23, 1987

[30] Foreign Application Priority Data

Sep. 25, 1986 [DE] Fed. Rep. of Germany ....... 3632527

[51] Int. Cl.⁴ .............................................. A61N 5/06
[52] U.S. Cl. ................................. 250/504 R; 128/377
[58] Field of Search ............ 250/492.1, 494.1, 504 R; 128/371, 372, 375, 376, 377, 395; D24/39; 297/457; 5/110, 111, 431, 432

[56] References Cited

U.S. PATENT DOCUMENTS

| | | | |
|---|---|---|---|
| 2,834,351 | 5/1958 | Garson | 128/372 X |
| 3,456,270 | 7/1969 | Weinstein et al. | 128/376 X |
| 4,055,867 | 11/1977 | Phillips | 128/376 X |
| 4,177,384 | 12/1979 | Wolff | 250/504 X |
| 4,234,977 | 11/1980 | Snow | 297/457 X |
| 4,300,249 | 11/1981 | Taylor | 128/377 X |
| 4,564,240 | 1/1988 | Thieme | 297/457 |
| 4,660,561 | 4/1987 | Nielson | 128/376 |

FOREIGN PATENT DOCUMENTS

| | | |
|---|---|---|
| 2204301 | 11/1972 | Fed. Rep. of Germany . |
| 2817908 | 11/1979 | Fed. Rep. of Germany . |
| 3231317 | 2/1984 | Fed. Rep. of Germany . |
| 3443045 | 5/1986 | Fed. Rep. of Germany ... 250/504 R |
| 8603682 | 7/1986 | World Int. Prop. O. ...... 250/504 R |

Primary Examiner—Eugene R. LaRoche
Assistant Examiner—Seung Ham
Attorney, Agent, or Firm—Peter K. Kontler

[57] ABSTRACT

A recliner pane of acrylic glass which is used to overlie the reflectors and the radiation sources in the support of a chair-like or cot-like tanning apparatus has a horizontal central section which supports the lower part of the back of the occupant, an upwardly sloping second section which supports the back and the head of the occupant and is disposed at one side of the central section, and a third section which slopes upwardly at the other side of the central section and supports the thighs of the occupant. A horizontal fourth section can be provided between the foot end of the pane and the third section to support the legs of the occupant. Such pane is sufficiently comfortable to enable the occupant to remain in an optimum position for tanning during a required interval of time.

18 Claims, 3 Drawing Sheets

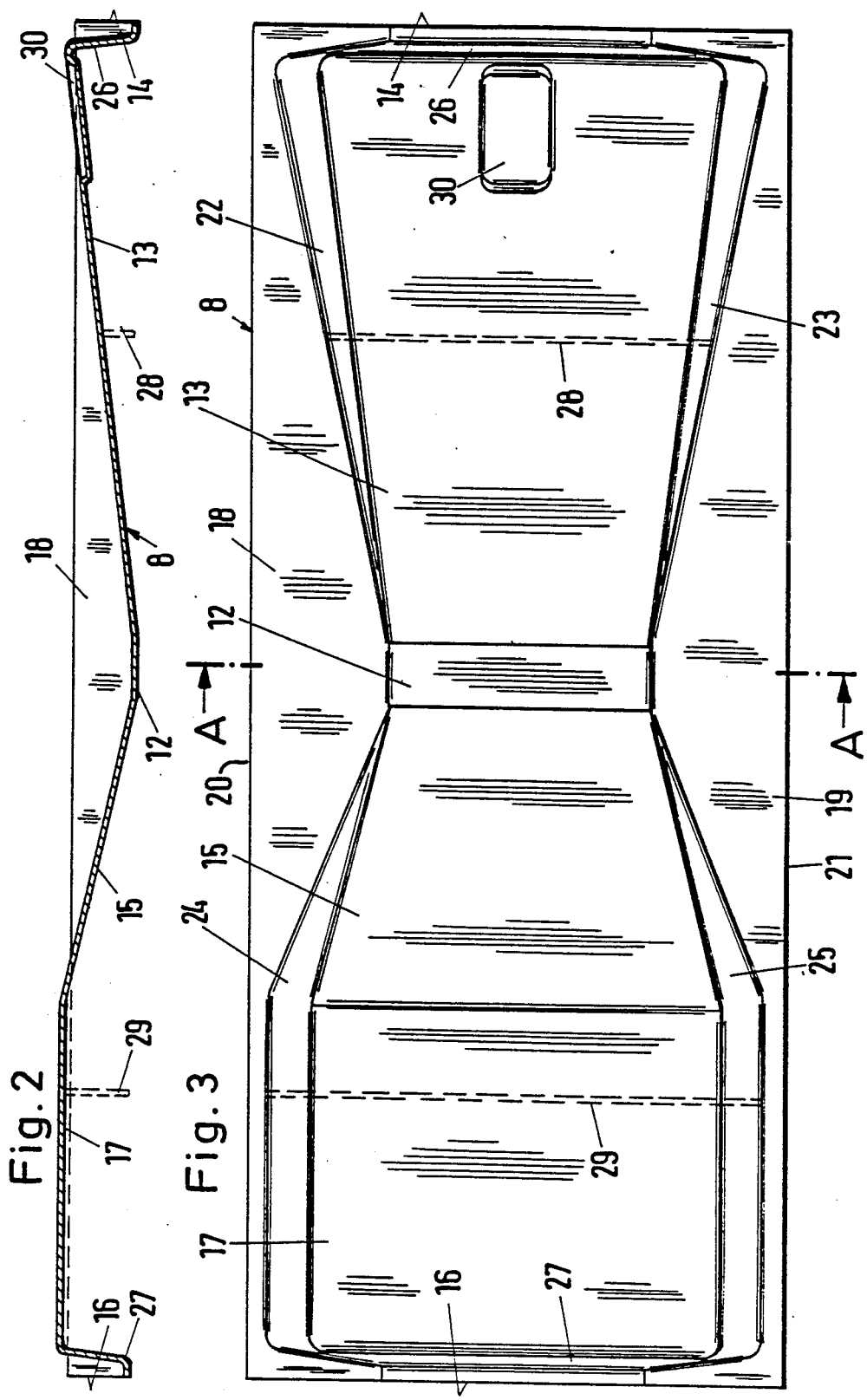

RECLINER PANE FOR TANNING APPARATUS

CROSS-REFERENCE TO RELATED CASE

The recliner pane of the present invention is similar to that which is disclosed in the commonly owned copending design patent application Ser. No. 071,611 filed July 8, 1987.

BACKGROUND OF THE INVENTION

The invention relates to tanning apparatus in general, and more particularly to improvements in tanning apparatus of the type wherein the occupant rests on a pane which, in turn, overlies one or more radiation sources.

It is well known to construct a tanning apparatus in the form of a lounge chair or easy chair wherein a floor- or ground-contacting support or frame carries a set of elongated lamps which emit radiation in the desired range of the spectrum and are normally mounted in front of suitable reflectors serving to direct radiation toward the body of the occupant of a flat plate-like pane which overlies the reflectors and the lamps. The material of the pane is such that it permits desirable radiation to penetrate therethrough, and the support is provided with mean for adequately bracing the pane from below.

Commonly owned German Offenlegungsschrift No. 32 31 317 discloses an apparatus which can be used for tanning or for medical purposes, particularly for use by patients suffering from psoriasis. The support of this apparatus carries a set of twelve parallel elongated radiation sources which are designed to emit radiation primarily in the UVA range and each of which is located in front of (above) a discrete reflector. The reflectors and the radiation sources are overlapped by an elongated radiation-transmitting pane including a longitudinally extending horizontal central portion and two marginal portions which slope upwardly from opposite sides of the central portion. The support is provided with means for bracing the pane from below along its longer sides and at least at one of its ends.

The pane consists of a relatively hard material, such as acrylic glass. This can create problems when the apparatus is to be used for a relatively long interval of time (for example, in excess of 15 minutes) because the pane causes discomfort so that the occupant must repeatedly shift her or his position which can affect the quality of treatment.

Attempts to enhance the comfort of the occupant include the provision of a mattress-like pad which overlies the pane and is in direct contact with the body of the occupant. Reference may be had to commonly owned German Pat. No. 26 01 939 which discloses a pad having air-filled pockets and consisting of a material which can be traversed by radiation in the UVA range of the spectrum.

German Auslegeschrift No. 22 04 301 discloses a chair which includes several mutually inclined portions and has a rigid portion for the thighs and legs and a resilient portion for the back and head of the occupant. This piece of furniture is not designed or intended for use as a tanning apparatus.

Commonly owned German Offenlegungsschrift No. 28 17 908 discloses a tanning apparatus wherein the pane is assembled of several transversely extending strips or bands which yield under the weight of the body of the occupant so that they conform to the outline of the body and are more comfortable than a rigid plate. A drawback of such proposal is that the cost of the composite pane and of mounting means therefor is considerable as well as that the useful life of such pane is much less than that of a rigid pane. Moreover, the occupant cannot ensure that each and every portion of the composite pane will be maintained at an optimum distance, or at an acceptable distance, from the nearest radiation source or sources.

OBJECTS AND SUMMARY OF THE INVENTION

An object of the invention is to provide a novel and improved radiation-transmitting pane which can be used in tanning and like apparatus as a superior, especially as a more comfortable, substitute for heretofore known and used panes.

Another object of the invention is to provide a pane which affords adequate comfort to the occupant even if its upper side is not padded or otherwise coated or overlapped with a yieldable material.

A further object of the invention is to provide a pane which can be used in certain existing tanning or analogous apparatus in lieu of presently used panes.

An additional object of the invention is to provide a pane which, even though made of a rigid material, affords as much comfort as a padded pane.

Still another object of the invention is to provide a tanning apparatus which embodies the above outlined pane.

A further object of the invention is to provide novel and improved means for adequately propping the improved pane on the support of a tanning apparatus.

An additional object of the invention is to provide a pane which enhances the appearance of the tanning apparatus and is sufficiently comfortable to enable the occupant to remain in a selected optimum position for tanning during a reasonably long interval of time, i.e., during the maximum interval which is recommended by a physician or by the maker of the apparatus.

Another object of the invention is to provide the pane with novel and improved means for supporting selected portions of the body of the occupant.

One feature of the invention resides in the provision of a preferably substantially rectangular recliner pane for use in tanning apparatus, particularly in cots, lounge chairs or easy chairs. The improved pane comprises a centrally located deepmost first section in the region of the lower part of the back of the occupant of the apparatus, and upwardly sloping second and third sections which flank the first section and respectively serve to support the back (and preferably also the head) and the thighs of the occupant.

The pane preferably further comprises two longitudinally extending marginal portions which flank all three sections and preferably have substantially parallel edge faces (these are the two longer sides of the rectangular pane). The marginal portions preferably slope upwardly from the first, second and third sections toward the respective edge faces. The pane can further comprise intermediate walls which connect the second and third sections with the marginal portions and are normally inclined with reference to the marginal portions and the sections. The pane preferably further comprises a fourth section which is disposed at a level above the first section and is integral with the third section and with the marginal portions and serves to support the legs of the occupant of the pane. The third section is disposed between the first and fourth sections, and all of the sections can be flat or nearly flat. This also applies for the marginal portions. The fourth section is or can be substantially horizontal and substantially parallel to the first section.

The pane can further comprise downwardly extending first and second end wall members which flank the second and fourth sections and have lower end portions which are or can be disposed at or close to the level of the first section. The second section is located between the first end wall member and the first section, and the third and fourth sections are located between the first section and the second end wall member.

At least one brace can be provided to extend from the underside of at least one of the sections. Such brace can have portions of different height, especially if it extends longitudinally of the pane. However, it is equally possible to provide at least one of the sections with at least one brace (e.g., a platelike element) which extends transversely of the pane. If the brace extends longitudinally of the pane (i.e., longitudinally of the respective section or sections), it is flanked by longitudinally extending radiation sources which are used in the apparatus to emit radiation passing through the pane and tanning the skin of the occupant. The brace which extends transversely of the pane is preferably provided at the underside of at least one of the second, third and fourth sections.

The second section can be provided with a recess in the region of the head of the occupant, and such recess can receive a removable cushion, preferably a cushion having marginal portions which extend laterally beyond the respective sides of the recess.

Another feature of the invention resides in the provision of a tanning apparatus which comprises a support, a plurality of radiation emitting elements in the support, and the aforementioned recliner pane which overlies the radiation emitting elements and whose material is selected with a view to ensure that it can permit penetration of certain ultraviolet and/or other radiation which is useful for tanning and/or healing purposes. Such apparatus can further comprise a second support at a level above the pane, and a plurality of radiation emitting elements which are carried by the second support and serve to direct radiation upon the occupant of the pane.

The novel features which are considered as characteristic of the invention are set forth in particular in the appended claims. The improved pane itself, however, both as to its construction and the mode of installing the same, together with additional features and advantages thereof, will be best understood upon perusal of the following detailed description of certain specific embodiments with reference to the accompanying drawing.

BRIEF DESCRIPTION OF THE DRAWING

FIG. 2 is a smaller-scale longitudinal vertical sectional view of the recliner pane;

FIG. 3 is a plan view of the recliner pane of FIG. 2;

DESCRIPTION OF THE PREFERRED EMBODIMENTS

Figure 1:
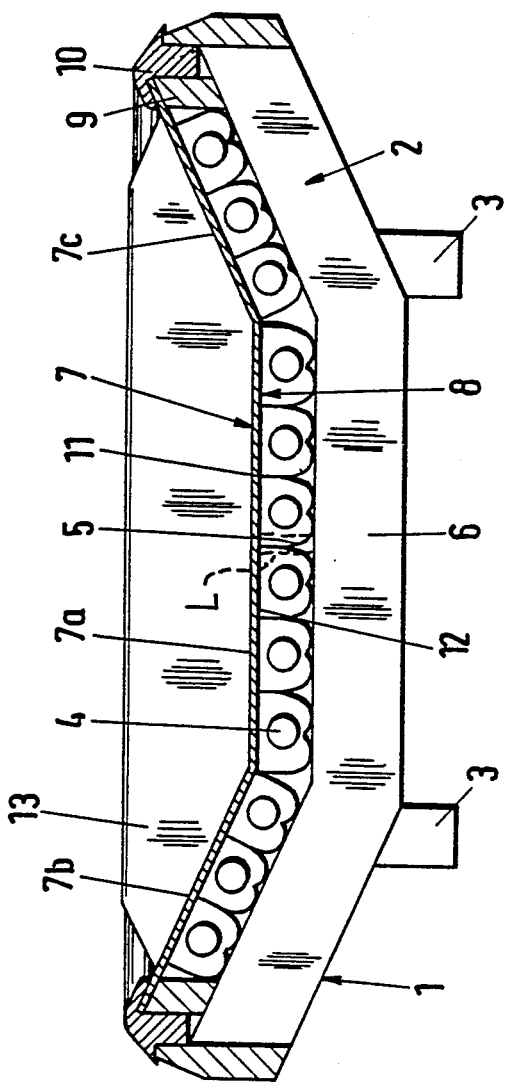
FIG. 1 is a transverse sectional view of a tanning apparatus which employs a recliner pane embodying the invention, the section being taken in the direction of arrows from the line A—A of FIG. 3.

FIG. 1 shows a tanning apparatus 1 which constitutes a cot, a lounge chair or an easy chair having a frame or support 2 for a set 7 of twelve longitudinally extending parallel radiation sources or lamps 4 each of which is partially surrounded by a trough-shaped reflector 5. The support 2 has ground or floor-contacting legs 3 and comprises several transversely extending carriers or beams 6 which directly support the reflectors 5. The radiation sources 4 and reflectors 5 form three groups including a centrally located group 7a of six parallel reflectors and lamps, a left-hand group 7b of three parallel reflectors and lamps, and a right-hand group 7c of three reflectors and lamps. The width of the set 7 is constant all the way from the head end to the foot end of the apparatus 1. Each radiation source 4 is or can constitute a fluorescent lamp with a sealed envelope for means which generate a low-pressure mercury discharge and with a coating for conversion of a portion at least of radiation into skin-tanning or psoriasis-healing radiation in a manner disclosed in numerous pending United States and foreign patent applications and in numerous United States and foreign patents of the applicant. The group 7a of radiation sources 4 and reflectors 5 is disposed in a substantially horizontal plane. The groups 7b and 7c are disposed in planes which flank and slope upwardly from the plane of the group 7a.

In accordance with a feature of the invention, the apparatus 1 further comprises a specially designed substantially rectangular recliner pane 8 which transmits useful radiation and overlies the upper edges 11 of the reflectors 5 in close or immediate proximity to the radiation sources 4. As shown in FIG. 3, the pane 8 has a constant width (between two parallel edge faces 20 and 21) and is elongated in a direction from the head end toward the foot end of the apparatus 1. The configuration of the underside of the pane 8 can closely conform to the configuration of the structure including the upper edges 11 of all reflectors 5, and the pane rests or can rest directly on such edges. The topmost or outermost parts of the two longitudinally extending marginal portions 18 and 19 of the pane 8 (these marginal portions define the edge faces 20, 21) are overlapped by longitudinally extending clamping or retaining strips 10 which cooperate with longitudinally extending supporting elements 9 to maintain the pane 8 in the position of FIG. 1. Thus, the marginal portions 18, 19 of the pane 8 rest on the supporting elements 9, and the longitudinally extending intermediate portions of the pane rest on the upper edges 11 of the reflectors 5.

As can be seen in FIGS. 1 to 3, the pane 8 comprises a deepmost first or central section 12 which is located at a lowermost level and rests on intermediate portions of the edges 11 forming part of reflectors 5 in the central group 7a. The section 12 is relatively narrow and serves to support the lower part of the back of the occupant of the pane 8. This section is or can be located in a substantially horizontal plane when the apparatus 1 is in use and the section 12 is flanked by an upwardly sloping second section 13 and an upwardly sloping third section 15, i.e., the sections 13, 15 are inclined relative to the first section 12 as well as relative to each other. The section 13 serves to support the back and the head of the occupant, and the section 15 is arranged to support the thighs of the person lying on the pane 8. The first section 12 has a rectangular outline. On the other hand, the width of each of the second and third sections 13, 15 increases in a direction away from the section 12, and the third section 15 merges into a horizontal or nearly horizontal fourth section 17 which has a rectangular or square outline and serves to support the legs of the occupant of the pane 8. The section 17 can be said to form part of the section 15 or vice versa.

The pane 8 further comprises the aforementioned marginal portions 18, 19 which flank the sections 12, 13, 15, 17 and slope upwardly from the first section 12 toward the respective edge faces 20, 21. Intermediate walls 22, 23 flank the section 13 and are integral with this section as well as with the respective marginal portions 18, 19. Similar or analogous intermediate walls 24, 25 are provided between the sections 15, 17 on the one hand and the marginal portions 18, 19 on the other hand. Still further, the pane 8 comprises a first end wall member 14 at the head end of the pane, and a second end wall member 16 at the foot end of the pane. The lowermost portions of the end wall members 14, 16 extend to or close to the level of the first section 12. FIG. 2 shows that a portion at least of the structure including the sections 13, 15 and 17 can extend to a level above one or both edge faces 20, 21; in the illustrated embodiment, the entire section 17 extends to a level above the edge faces 20 and 21.

All four sections of the pane 8 are or can be substantially flat. The marginal portions 18, 19 overlie in part the groups 7b and 7c of reflectors 5 and radiation sources 4. The purpose of the intermediate walls 22-25 is to compensate for differences in the levels of the adjacent portions of sections 13, 15, 17 on the one hand and the marginal portions 18, 19 on the other hand.

The end wall member 14 includes a downwardly extending portion 26 which is closely or immediately adjacent a shallow recess 30 in the upper side of the second section 13. The end wall member 16 includes a downwardly extending portion 27. The lowermost parts of the portions 26, 27 are suitably shaped to come into relatively large-area contact with the adjacent portion of the support 2. The portions 26, 27 alternate with the supporting elements 9 in the circumferential direction of the pane 8 and ensure that the latter is reliably located in an optimum position with reference to the support 2. As mentioned above, the pane 8 is further propped by the edges 11 of the reflectors 5. If it is desired to even more reliably mount the pane 8 on the support 2, one or more sections of the pane can be provided with one or more braces or legs which prop the respective section or sections from below. FIG. 2 shows, by way of example and by broken lines, a first brace or leg 28 which extends transversely of the section 13 and from the underside of this section to the edges 11 of the reflectors 5 below it, and a second brace or leg 29 which is parallel to the brace 28 and extends from the underside of the section 17 to rest on the adjacent portions of edges 11. A further brace L (indicated in FIG. 1 by broken lines) can extend longitudinally of the pane 8 from the undersides of the sections 13, 15, 17 to rest on the two median edges 11 in the central group 7a. This ensures that the pane 8 can carry the weight of a heavyset person if it is made of a relatively thin material, particularly a synthetic plastic material which transmits radiation in the desired range or ranges of the spectrum. The brace or braces are or can be integral with the pane 8 and can be made of the same material, e.g., acrylic glass. Alternatively, such brace or braces can be produced separately and are then affixed to the underside(s) of the selected section(s) by a suitable adhesive. Portions of the braces 28, 29, L have different heights due to the inclination of the respective sections relative to the adjacent groups 7a, 7b, 7c of the set 7 of reflectors 5 and radiation sources 4.

Figure 4:
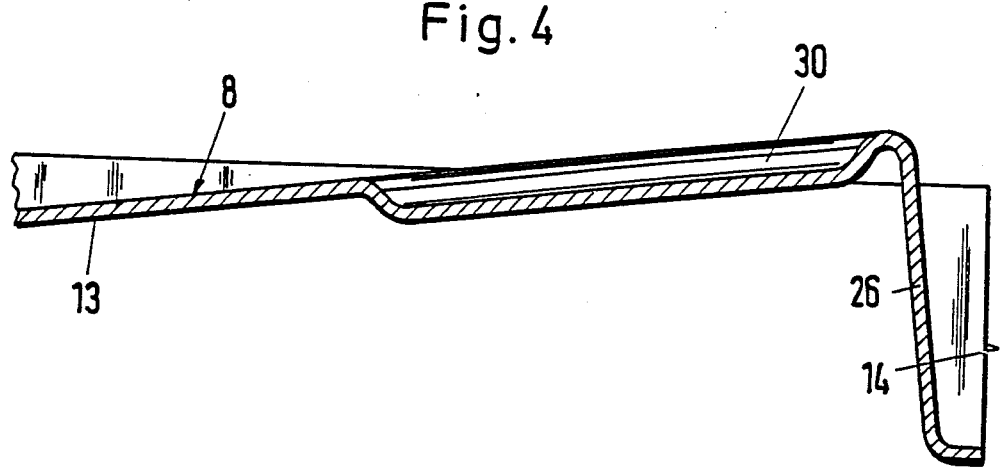
FIG. 4 is an enlarged view of a detail in FIG. 2.
Figure 5:
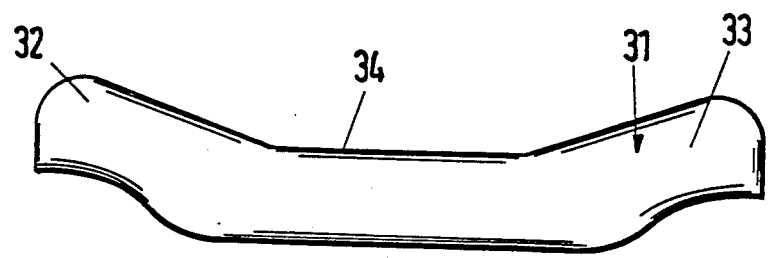
FIG. 5 is an elevational view of a cushion which can be used with the improved recliner pane.

The recess 30 is shown on a larger scale in FIG. 4. This recess is located beneath the head of the person occupying the pane 8 and is preferably overlapped by a suitable cushion 31 (see FIG. 5) having marginal portions 32 and 33 which slope upwardly from and flank a median portion 34. The marginal portions 32, 33 preferably extend beyond the top and bottom ends of the recess 30. The cushion 31 can be made of or can contain a polyurethane foam. The dimensions of this cushion can be selected in such a way that all of its marginal portions extend laterally beyond the recess 30 or that two of its marginal portions extend beyond the recess 30 in directions toward the edge faces 20 and 21. The provision of two or more marginal portions which project beyond the recess 30 ensures that the central portion 34 is reliably held in the recess even if the cushion 31 is not bonded to the pane 8.

Figure 6:
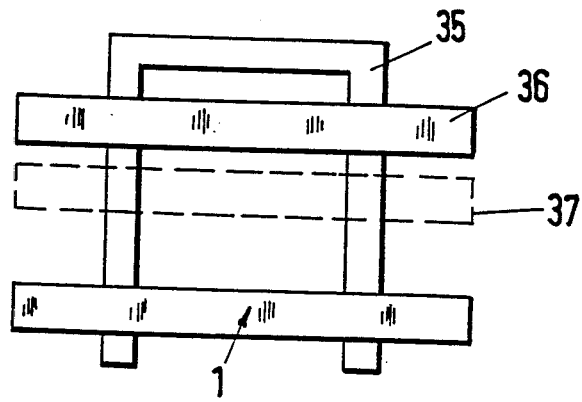
FIG. 6 is a schematic view of a modified apparatus which employs the structure of FIGS. 1–5 and an overhead support for additional radiation sources.

FIG. 6 shows schematically a modified apparatus which includes the apparatus 1 of FIGS. 1–5 and a second support 36 which is analogous to the support 2 and serves to carry a second set of radiation sources similar to or identical with the lamps 4. The support 36 is movable up and down and/or is otherwise adjustable relative to a frame 35 so as to enable the user of the tanning apparatus to lie down on the pane 8 of the apparatus 1 and to thereupon lower the support 36 (e.g., to the position 37 which is shown in FIG. 6 by broken lines) so that the occupant of the pane 8 can receive a tan from below (through the pane 8) as well as from above. The modified apparatus of FIG. 6 can comprise a motor-driven mechanism which can raise or lower and/or otherwise adjust the position of the support 36 relative to the support of the apparatus 1.

As a rule, the occupant of the pane 8 in the apparatus of FIG. 6 will face upwardly toward the support 36 and the radiation sources therein.

An important advantage of the improved pane 8 and of the apparatus which embodies such pane is that it is much more comfortable to the occupant than a substantially flat or a substantially trough-shaped pane. This is believed to be attributable to the fact that the central portion (including the lower part of the back) of the body of the person resting on the pane 8 is located at a level below the levels of the other portions of the body, and that the sections 13 and 15 (which respectively support the back and the head on the one hand and the thighs on the other hand) slope gradually from the section 12 toward the respective end wall elements 14 and 16. Such configuration and mutual inclination of the sections 12, 13 and 15 enables the occupant to relax in a natural position, and the occupant is thus capable of remaining in prone position for the interval of time (e.g., 15–30 minutes) which is prescribed or advisable for a tanning session.

The purpose of the marginal portions 18, 19 is to ensure that the respective edges of the pane 8 can rest on the adjacent supporting elements 9 all the way between the end wall members 14 and 16 and that the pane 8 cooperates with the support to reduce the likelihood of penetration of contaminants into the reflectors 5. The inclination of intermediate walls 22-25 with reference to the adjacent sections 13, 15, 17 and marginal portions 18, 19 contributes to more satisfactory rigidity of the pane 8, i.e., to its ability to resist deformation even if it must carry a substantial weight.

The fourth section 17 is optional, i.e., the section 15 could extend all the way from the section 12 to the end wall member 16. An advantage of the section 17 is that it offers additional comfort to the occupant in that it is inclined with reference to the section 15 and thus conforms to the natural angle between the thighs and the legs of the occupant.

Another advantage of the improved apparatus is that it can employ the support, the radiation sources and the reflectors of certain types of available apparatus, i.e., all that is necessary is to furnish the pane 8 and to provide the support with means for adequately bracing the pane from below if the engagement between the pane on the one hand and the supporting elements 9 and edges 11 of the reflectors 5 on the other hand does not always suffice to ensure that the pane will stand the applied stresses and/or that the support can readily carry the pane without any damage to its parts. The end wall members 14, 16 whose lowermost portions extend to the general level of the section 12 ensure that the pane 8 can be used in conjunction with available supports, i.e., that it can come to rest on a plurality of coplanar and substantially horizontal parts, just as a flat pane of the type used in conventional tanning apparatus. The marginal portions 18, 19 of the pane 8 are or can be designed in such a way that they can come to rest on certain parts of an available support so that a conventional apparatus can be rendered more comfortable by the simple expedient of replacing a conventional pane with the pane of the present invention.

The braces 28, 29 and L are optional. They can be provided if at least one of the sections 13, 15, 17 extends to a level above the edge face 20 and/or 21, i.e., if at least one of these sections is spaced apart from the parts below it so that it requires or can stand additional propping. The section 13, 15 and/or 17 will be caused to extend above the level of the edge face 20 and/or 21 if this contributes to the comfort of the occupant. Such configuration of the pane 8 is possible because it is adequately supported all along its edges and, if necessary, its intermediate portions can be supported from below not only by the edges 11 of the reflectors 5 but also by one or more braces such as those shown at 28, 29 and L.

A pane with flat or substantially flat sections 12, 13, 15 and 17 (or with one, two or three substantially flat sections) is preferred at this time because such design contributes to lower cost of the pane. Moreover, such sections can be readily supported from below by all of the adjacent edges 11.

The recess 30 for the cushion 31 is optional. It is normally provided since the configuration of the pane 8 departs from that of a flat plate anyway so that the provision of such recess adds little to the cost of the pane. The utilization of a cushion 31 with marginal portions which extend beyond the recess 30 is desirable because, when placed into the recess 30, such cushion defines a depression which enhances the comfort to the head which rests on the central portion 34 of the cushion.

The improved apparatus can be modified in a number of ways without departing from the spirit of the invention. For example, the support 2 can include upwardly extending partitions which are disposed between neighboring reflectors 5 to serve as abutments for the underside of the pane 8 so that the latter need not rest directly or exclusively on the edges 11 of the reflectors 5. Furthermore, two or more neighboring radiation sources 4 can be installed in front of a common reflector, i.e., the number of radiation sources can exceed the number of reflectors, so that the underside of the pane 8 then rests on a reduced number of edges 11. The aforementioned partitions can be used in addition to or in lieu of columns which extend upwardly from the support 2 and/or downwardly from the pane 8 to brace the pane from below. The partitions can be bonded or otherwise secured to the underside of the pane 8 in lieu of being integral with or connected to the support 2. The apparatus can employ low-pressure mercury discharge lamps or high-pressure lamps and/or other types of radiation sources. This also holds true for the radiation sources in the overhead support 36 of FIG. 6. The substantially flat section 12, 13, 15 and/or 17 of the pane 8 can be replaced with a curved (concave or convex) section if such configuration even further enhances the comfort of the occupant of the pane and/or enables the pane to more accurately conform to the outline of the structure including the edges 11 of the reflectors 5. The width of the section 12 (as measured in the longitudinal direction of the pane 8) can be reduced to less than that shown in FIGS. 2 and 3, e.g., to a minute fraction of the illustrated width so that such narrowed section 12 then merely constitutes a junction or possibly an extremely narrow transition zone between the lowermost portions of the sections 13 and 15. Still further, the section 12 need not be located exactly midway between the end wall members 14 and 16 but can be nearer to the member 14 or 16.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A recliner pane for use in tanning apparatus, such as lounge chairs, said pane consisting of a relatively hard material and comprising a substantially centrally located deepmost first section in the region of the lower part of the back of the occupant of the apparatus; upwardly sloping second and third sections flanking said first section and respectively arranged to support the back and the thighs of the occupant; two marginal portions flanking said sections and having substantially parallel edge faces, a portion at least of at least one of said sections extending to a level at least close to at least one said edge faces; and intermediate walls connecting said second and third sections with each of said marginal portions.

2. The pane of claim 1, wherein said marginal portions slope upwardly from said first section toward the respective edge faces.

3. The pane of claim 1, further comprising a fourth section disposed at a level above said first section, integral with said third section and with said marginal portions, and arranged to support the legs of the occupant, said third section being disposed between said first and fourth sections and all of said sections being substantially flat.

4. The pane of claim 3, wherein said marginal portions are substantially flat.

5. The pane of claim 3, wherein a portion at least of at least one of said second, third and fourth sections extends to a level above at least one of said edge faces.

6. The pane of claim 1, further comprising a fourth section disposed at a level above said first section, integral with said third section and arranged to support the legs of the occupant, said third section being disposed between said first and fourth sections.

7. The pane of claim 6, wherein said fourth section is substantially horizontal.

8. The pane of claim 1, further comprising downwardly extending first and second end wall members flanking said second and third sections and having lower end portions disposed at or close to the level of said first section, said second section being located between said first end wall member and said first section, said third section being located between said first section and said second end wall member.

9. The pane of claim 1, wherein at least one of said sections has an underside and a brace extending from said underside.

10. The pane of claim 9, wherein said brace has portions of different height.

11. The pane of claim 9, wherein said brace extends transversely of said sections so that it is traversed by longitudinally extending radiation sources of the apparatus embodying the pane.

12. The pane of claim 9, wherein said at least one section is one of said second and third sections, said brace extending downwardly at least close to the level of said first section.

13. The pane of claim 12, wherein said brace extends substantially longitudinally of said sections.

14. The pane of claim 1, wherein said second section includes a recess in the region of the head of the occupant.

15. The pane of claim 14, further comprising a cushion in said recess.

16. The pane of claim 15, wherein said cushion includes marginal portions extending beyond said recess.

17. A tanning apparatus comprising a support; a plurality of radiation emitting elements in said support; and an elongated radiation transmitting recliner pane overlying aid elements and consisting of a relatively hard material, said pane including a substantially centrally located deepmost first section in the region of the lower back of the occupant of the apparatus, upwardly sloping second and third sections flanking said first section and respectively arranged to support the back and the thighs of the occupant, two marginal portions flanking said sections and having substantially parallel edge faces, and intermediate walls connecting said second and third sections with each of said marginal portions, said radiation emitting elements extending longitudinally of said pane.

18. The apparatus of claim 17, further comprising a second support at a level above said pane, and a plurality of radiation emitting elements carried by said second support and arranged to direct radiation upon the occupant of said pane.

* * * * *